US011998684B2

(12) United States Patent
Goodwin et al.

(10) Patent No.: US 11,998,684 B2
(45) Date of Patent: Jun. 4, 2024

(54) DOSING SYSTEM FOR A NEBULIZER

(71) Applicant: VECTURA DELIVERY DEVICES LIMITED, Wiltshire (GB)

(72) Inventors: Paul Goodwin, Cambridgeshire (GB); Andreas Mark Meliniotis, Cambridgeshire (GB); Roger William Clarke, Cambridgeshire (GB); Tobias Kolb, Gauting (DE)

(73) Assignee: VECTURA DELIVERY DEVICES LIMITED, Chippenham (GB)

( * ) Notice: Subject to any disclaimer, the term of this patent is extended or adjusted under 35 U.S.C. 154(b) by 1198 days.

(21) Appl. No.: 16/624,334

(22) PCT Filed: Jun. 19, 2018

(86) PCT No.: PCT/EP2018/066296
§ 371 (c)(1),
(2) Date: Dec. 19, 2019

(87) PCT Pub. No.: WO2018/234324
PCT Pub. Date: Dec. 27, 2018

(65) Prior Publication Data
US 2020/0147326 A1 May 14, 2020

(30) Foreign Application Priority Data
Jun. 21, 2017 (EP) .................................... 17177225

(51) Int. Cl.
*A61M 15/00* (2006.01)

(52) U.S. Cl.
CPC .... *A61M 15/0065* (2013.01); *A61M 15/0085* (2013.01); *A61M 2202/0468* (2013.01)

(58) Field of Classification Search
CPC ........ A61M 11/00; A61M 11/005–008; A61M 11/06; A61M 15/00;
(Continued)

(56) References Cited

U.S. PATENT DOCUMENTS

2007/0068593 A1 3/2007 Behar et al.
2016/0193434 A1* 7/2016 Gleixner ................ A61M 11/06 128/200.14

FOREIGN PATENT DOCUMENTS

CN 102596296 A * 7/2012 ........ A61M 15/0085
CN 204995925 1/2016
(Continued)

OTHER PUBLICATIONS

European Search Report for Application No. 17177225.4 dated Dec. 6, 2017.
(Continued)

*Primary Examiner* — Elliot S Ruddie
(74) *Attorney, Agent, or Firm* — Ryan P. Cox; Todd Lorenz

(57) ABSTRACT

The invention provides a dosing system for an inhalation device, comprising a filling chamber (10); a reservoir chamber (31) which supplies liquid (3) to an aerosol generator (301); and a plunger (20) which includes an overflow chamber (25) and which is pivotable about a hinge (50). The filling chamber has an inner wall (12) which is higher on the side adjacent to the hinge than on the opposite side. When the filling chamber is filled with liquid and the plunger is pivoted into the filling chamber, part of the liquid is displaced over the lower side (17) of the inner wall into the reservoir chamber and some or all of the remaining liquid is displaced into the overflow chamber. The invention also provides an inhalation device comprising the dosing system and a method for dosing liquid to the inhalation device.

17 Claims, 12 Drawing Sheets

(58) Field of Classification Search

CPC ........... A61M 15/0021–0026; A61M 15/0028; A61M 15/0065–0066; A61M 15/0085; A61M 2205/8206; A61M 15/02; A61M 2039/2426; A61M 2039/248; A61M 2205/3386; A61M 2205/584; A61M 39/24; A61M 2202/0468; A61M 2202/0007; B05B 17/0623; B05B 17/0638

See application file for complete search history.

(56) References Cited

FOREIGN PATENT DOCUMENTS

| | | | |
|---|---|---|---|
| EP | 0388106 | 9/1990 | |
| EP | 1205199 | 5/2002 | |
| JP | 3563467 | 9/2004 | |
| WO | 2003061741 | 7/2003 | |
| WO | 2011055243 | 5/2011 | |
| WO | WO-2011055243 A1 * | 5/2011 | .......... A61M 11/005 |
| WO | 2015022436 | 2/2015 | |

OTHER PUBLICATIONS

International Search Report and Written Opinion for PCT Application No. PCT/EP2018/066296 dated Jul. 31, 2018.

* cited by examiner

DOSING SYSTEM FOR A NEBULIZER

CROSS-REFERENCE TO RELATED APPLICATIONS

This application is a United States national stage of International Application No. PCT/EP2018/066296, filed Jun. 19, 2018, which was published as International Publication No. WO 2018/234324, and which claims benefit of European Application No. 17177225.4, filed Jun. 21, 2017, the entire contents of which are hereby expressly incorporated herein by reference.

Nebulizers are inhalation devices that convert a liquid formulation, which usually contains an active agent, into an inhalable aerosol (i.e. a dispersion of fine liquid droplets), for example by means of an ultrasonic aerosol generator, a jet or a vibrating mesh. The aerosol is delivered to the lungs by inhalation, particularly for the treatment of respiratory diseases such as asthma and cystic fibrosis.

Nebulizers differ from other inhalation devices such as dry powder inhalers, pressurized metered dose inhalers and soft mist inhalers in that they operate continuously. Treatment may take place during a few breaths or for an extended period of time (e.g. up to about 45 minutes). During this time, the nebulizer emits aerosol either constantly or in pulses which may be adapted to the user's breathing pattern; for example, aerosol generation may be triggered by the onset of inhalation. Thus, nebulizers do not per se emit metered amounts of aerosols, and unless switched off, they produce aerosol until the liquid has all been used up.

Consequently, it is necessary to dose the correct amount of liquid formulation to the aerosol generator. One way of doing this is to use pre-filled single-use cartridges which are completely emptied into the nebulizer, so that the liquid is all nebulized. However, the dosing flexibility of such cartridges is limited because a particular cartridge can only dose one fixed volume. Thus when the prescribed amount of medicine to be inhaled does not match the volume of the liquid supplied in the container, it is necessary to ensure that only the prescribed amount is delivered in aerosol form.

BACKGROUND TO THE INVENTION

A dosing system for this purpose is disclosed in EP 1 465 692, having a metering chamber and a second (overflow) chamber. The metering chamber defines the volume of the substance to be nebulized and is arranged so as to feed this volume to the aerosol generator, while any substance poured into the metering chamber in excess of its volume is received and retained in the second chamber. In other words, the metering chamber is filled until the liquid overflows into the second chamber, and only the metered volume inside the metering chamber is subsequently nebulized. This has the disadvantage that any changes in the prescribed dose would require complete replacement of the metering chamber assembly. Furthermore, the metering system is not suitable for metering very small amounts of liquids which are substantially affected by adhesive and cohesive forces and do not easily flow from one chamber to another.

Further dosing systems are disclosed in EP 1 205 199 and EP 2 496 293. Both of these have a filling chamber with a wider upper portion and a narrower lower portion that is closed by a valve at its bottom end. A plunger is inserted into the filling chamber from its wider upper end along the chamber's longitudinal axis. Once the plunger reaches the narrower lower portion, a seal is formed between the plunger and the walls of the lower portion, so that liquid can no longer be displaced upwards into the upper portion. Upon continued insertion of the plunger, the liquid in the lower portion is pushed out through the valve, thus dosing a metered volume, while the excess liquid remains in the upper portion above the seal. The dispensed volume can be altered by changing the volume and/or the extent of insertion of the plunger. The plunger actively displaces the liquid to be dosed, thus overcoming the issues associated with dispensing small amounts of viscous liquids. When the plunger is retracted, the excess liquid can flow into the lower portion and could be pushed out through the valve if the plunger is re-inserted. This is advantageous when the filling chamber is deliberately filled with a multi-dose amount of liquid and the dosing system is supposed to be actuated repeatedly. However, it is highly undesirable in cases where such re-dosing is unintended and may even be harmful due to overdosing. For example, only small amounts (substantially less than the supplied volume) of liquid formulation may be intended to be administered to neonates, infants, or children, or to subjects with an improving health-condition. For instance, the liquid formulation may only be available in ampoules containing 1 mL or more, while the subject should receive only 200 μL. The dosing systems of EP 1 205 199 and EP 2 496 293 would allow the unintended administration of an extra 800 μL to the patient.

WO 2015/022436 discloses a dosing system having both an overflow chamber and a plunger which forms a seal with the filling chamber, in order to isolate the excess volume of liquid that is not supposed to be administered to the user, so that it cannot be re-dosed accidentally. Two general types of dosing system are disclosed. In the first, the filling chamber is separated from the aerosol generator chamber by a closing means, such as a duckbill valve. Liquid is poured into the filling chamber, where it is retained by the valve. The plunger is inserted, thereby displacing some of the liquid into the overflow chamber. The plunger must then form a seal with the filling chamber wall, so that it can apply pressure to the liquid in order to open the valve and supply a metered volume of liquid to the aerosol generator chamber. In the second type of dosing system, there is no valve between the filling chamber and aerosol generator; nonetheless a seal between the plunger and the filling chamber is necessary, in order to isolate a metered volume of liquid. However, the requirement of forming a seal means imposes requirements on the materials from which the plunger and/or filling chamber are made, and/or require additional components, such as O rings.

When the user opens the lid of the dosing system (as in EP 1 465 692) and/or removes the plunger (as in EP 1 205 199, EP 2 496 293 and most of the embodiments of WO 2015/022436) after nebulization, the excess liquid is visible to the user. As a result, the user may mistakenly think that they have not received the full dose, and thus may try to use the excess, which could result in an overdose. Alternatively, the user might understand that they have received the correct dose, but then try to use the excess liquid for a subsequent dose, in order not to waste the liquid, which could result in the incorrect dose and also lead to contamination.

Thus there is a need for an improved dosing system which can accurately dispense pre-determined volumes of liquid, especially small amounts, which does not suffer from the drawbacks of the previous dosing systems.

BRIEF DESCRIPTION OF THE INVENTION

In a first aspect, the present invention provides a dosing system for an inhalation device, comprising:

(a) a filling chamber for receiving a liquid to be aerosolized, the filling chamber having an outer wall, a base and an inner wall which defines an outlet opening, (b) a reservoir chamber for supplying liquid an aerosol generator, (c) a plunger which is mounted on a hinge and which includes an overflow chamber, wherein the inner wall of the filling chamber is higher on the side adjacent to the hinge than on the opposite side so that when the filling chamber is filled with liquid and the plunger is inserted into the filling chamber by pivoting it about the hinge, part of the liquid is displaced by the plunger over the lower side of the inner wall of the filling chamber and into the reservoir chamber via the outlet opening, and some or all of the remaining liquid is displaced by the plunger from the filling chamber into the overflow chamber.

Preferably the dosing system comprises a cap located above the filling chamber outlet opening which prevents liquid from being supplied directly into the reservoir chamber.

Preferably the plunger has an inner wall and an outer wall, and at least part of the inner and outer walls of the filling chamber and the plunger are curved in profile so that there is a close fit between the inner walls of the plunger and filling chamber when the plunger is fully inserted into the filling chamber.

Preferably the hinge is provided with a detent mechanism which resists the pivoting motion of the plunger in order to prevent the plunger from being inserted rapidly, which could cause some of the liquid to splash out of the filling chamber.

Preferably the top of the lower side of the inner wall of the filling chamber and the top of the inner wall of the plunger are at the same height when the plunger is fully inserted.

Preferably a partition is located inside the inner wall of the filling chamber, which more preferably is parallel to the hinge and even more preferably extends vertically down into the reservoir chamber. The liquid which is displaced from the filling chamber when the plunger is inserted flows over the lower part of the inner wall and down the corresponding side of the reservoir chamber. The higher part of the inner wall prevents liquid from flowing down on the opposite side, so that air is displaced upwardly on that side of the reservoir chamber. This prevents the formation of an airlock, i.e. a trapped bubble of air at the bottom of the reservoir chamber.

Conveniently, the cap can be formed as an extension of the partition.

Preferably the overflow chamber has a cover on the side adjacent to the hinge, which closes the top of the overflow chamber on this side. More preferably the cover comprises a semi-annular wall and a semi-annular floor which preferably slopes slightly downwards from the outer wall of the overflow chamber adjacent to the hinge towards the opposite side of the overflow chamber (when the plunger is inserted). Thus, as the plunger is inserted, excess liquid is displaced over the lower side of the filling chamber inner wall and enters the uncovered part of the overflow chamber. The higher part of the filling chamber inner wall, together with the cover wall prevents liquid from flowing onto the top of the cover floor, or at least minimizes the amount of liquid that flows on to the top of the cover floor. Nonetheless, the slope of the cover floor guides any liquid which passes over or round the higher part of the filling chamber inner wall, or over the filling chamber outer wall, back down the slope towards the uncovered part of the over flow chamber opening and into the overflow chamber. Moreover, when the plunger is opened after nebulization has been completed, the cover floor is in a generally vertical orientation. In this position, the cover prevents liquid from flowing out of the overflow chamber. The cover closes enough of the top of the overflow chamber so that the liquid cannot flow out when the plunger is pivoted into the open position.

Preferably the plunger has a lid which covers the top of, and prevents direct access to, the overflow chamber, so that liquid cannot be filled directly into the overflow chamber, and so that the excess liquid is not visible to the user after nebulization. The lid is preferably fixed so that it is difficult for the user to access the overflow chamber. In order to allow the overflow chamber to be emptied and cleaned after nebulization has been completed, there is preferably an opening between the lid and the top of the overflow chamber. Preferably the opening is formed without a spout or other means of facilitating pouring out of the liquid, so that it is possible, but somewhat awkward, for the user to empty the overflow chamber. This emphasizes to the user that the excess liquid is not intended to be re-used.

Alternatively, the lid may be removable or openable, which facilitates emptying and cleaning of the overflow chamber after use. For example, the overflow chamber may be separately pivotable. Preferably the overflow chamber and lid have clip formations so that when the lid is closed, it becomes attached to the overflow chamber.

Preferably the overflow chamber corresponds to the size and shape of the filling chamber, so that the plunger forms a close fit and preferably occupies substantially the whole of the filling chamber when inserted. Nonetheless, when the filling chamber has an inner wall, there is preferably a small gap between the inner wall of the filling chamber and plunger (when inserted), through which the liquid displaced from the filling chamber flows. Preferably the gap is from 0.1 to 0.2 mm in width, such as about 0.15 mm.

Preferably the filling chamber and overflow chamber are generally annular in shape. Preferably the plunger is shaped so that it cannot be inserted into the reservoir chamber.

Preferably the filling chamber and the plunger are made from a rigid material, such as a rigid plastic.

In a second aspect, the present invention provides an inhalation device comprising the dosing system of the first aspect of the invention.

Preferably the inhalation device comprises an aerosol head and a base unit which are detachably connectible with each other, and wherein the aerosol head comprises the dosing system. More preferably, the aerosol head and base unit have complementary male and female features which interlock to provide a recognition system, for example, the base unit has two pegs of different sizes and the aerosol head has two corresponding holes.

In a third aspect, the present invention provides a method for dosing liquid to an inhalation device according to the second aspect of the invention, the method comprising supplying a liquid to be aerosolized to the filling chamber; and inserting the plunger into the filling chamber so that part of the liquid is displaced over the lower side of the inner wall of the filling chamber and into the reservoir chamber, and some or all of the remaining liquid is displaced into the overflow chamber.

DETAILED DESCRIPTION OF THE INVENTION

The present invention is further described with reference to the drawings, in which.

LIST OF NUMERICAL REFERENCES USED IN THE FIGURES

Figure 1:
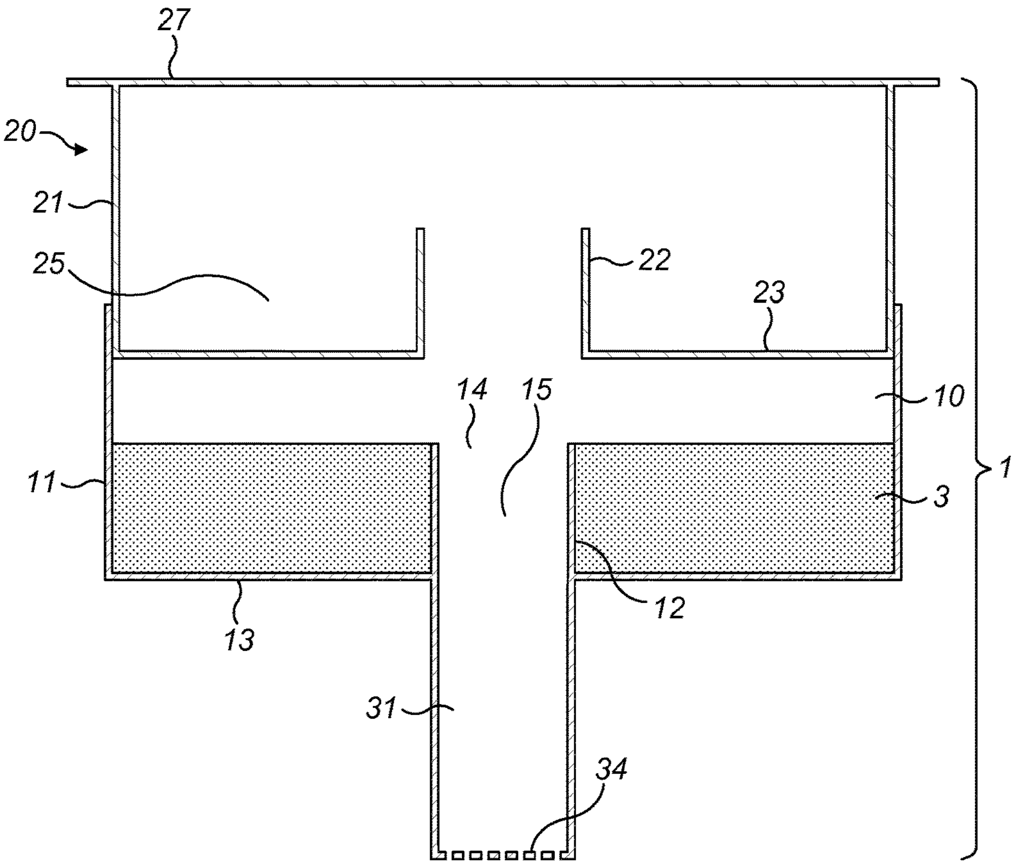
FIGS. 1, 2, 3 and 4 illustrate the general principle of a dosing system

| | |
|---|---|
| 1 | Dosing system |
| 3 | Liquid |
| 10 | Filling chamber |
| 11 | Filling chamber outer wall |
| 12 | Filling chamber inner wall |
| 13 | Filling chamber base |
| 14 | Filling chamber outlet opening |
| 15 | Central space |
| 16 | Higher side of inner wall |
| 17 | Lower side of inner wall |
| 20 | Plunger |
| 21 | Plunger outer wall |
| 22 | Plunger inner wall |
| 23 | Plunger base |
| 25 | Overflow chamber |
| 26 | Gap |
| 27 | Lid |
| 28 | Overflow chamber outlet opening |
| 31 | Reservoir chamber |
| 34 | Perforated membrane |
| 35 | Partition |
| 37 | Cap |
| 50 | Hinge |
| 51 | Curved region of filling chamber inner wall |
| 52 | Curved region of plunger inner wall |
| 53 | Straight region of filling chamber inner wall |
| 54 | Straight region of plunger inner wall |
| 55 | Cut-away region |
| 56 | Curved region of filling chamber outer wall |
| 57 | Curved region of plunger outer wall |
| 61 | Cover |
| 62 | Cover floor |
| 63 | Cover wall |
| 64 | Uncovered region of overflow chamber |
| 100 | Base unit |
| 102 | Air outlet opening |
| 103 | Groove |
| 104 | Base unit key lock members |
| 106 | Indentation |
| 140 | Pegs |
| 200 | Mouthpiece |
| 201 | Air inlet opening |
| 202 | Lateral opening |
| 203 | Aerosol outlet opening |
| 204 | Positioning member |
| 300 | Aerosol head |
| 301 | Aerosol generator |
| 303 | Aerosol head key lock members |
| 306 | Transducer body |
| 308 | Piezoelectric member |
| 310 | Filling chamber |
| 328 | Screw thread |

-continued

| | |
|---|---|
| 331 | Reservoir |
| 334 | Perforated membrane |
| 340 | Holes |

FIGS. 1 to 4 (not according to the invention) illustrate the general principle of a dosing system. The dosing system 1 has a filling chamber 10 for receiving the liquid 3 to be nebulized. The filling chamber has an outer wall 11, an inner wall 12 and a base 13, and is open at its upper end.

The outer and inner walls are circular (when viewed from above), so that the filling chamber 10 is annular. The top of the inner wall 12 forms an outlet opening 14. The inner wall 12 also defines a central space 15 which lies inside it. Situated beneath the central space 15 is a reservoir chamber 31 which supplies liquid to an aerosol generator. The inner wall 12 therefore acts as a barrier which prevents liquid from flowing from the filling chamber to the reservoir chamber.

The aerosol generator may be, for example, a vibrating perforated membrane 34. The membrane 34 has a large number of holes, typically from about 1 μm to about 10 μm in diameter at the exit (aerosol) side of the membrane. Without vibration of the membrane, the balance of pressures, the shape of the holes and the nature of the material used for the membrane are such that the liquid does not seep out through the membrane. However, vibration of the membrane leads to the formation and emission of aerosol droplets through the holes.

The dosing system has a plunger 20 for insertion into the filling chamber. The plunger has an outer wall 21, an inner wall 22 and a base 23 which connects the outer and inner walls. Together, the walls and base form an overflow chamber 25. In contrast to some of the dosing systems of WO 2015/022436, the plunger is not (and cannot be) inserted into the reservoir chamber. This is advantageous because there is no risk of the plunger being forced too far into the reservoir chamber and coming in to contact with the membrane 34.

Figure 3:
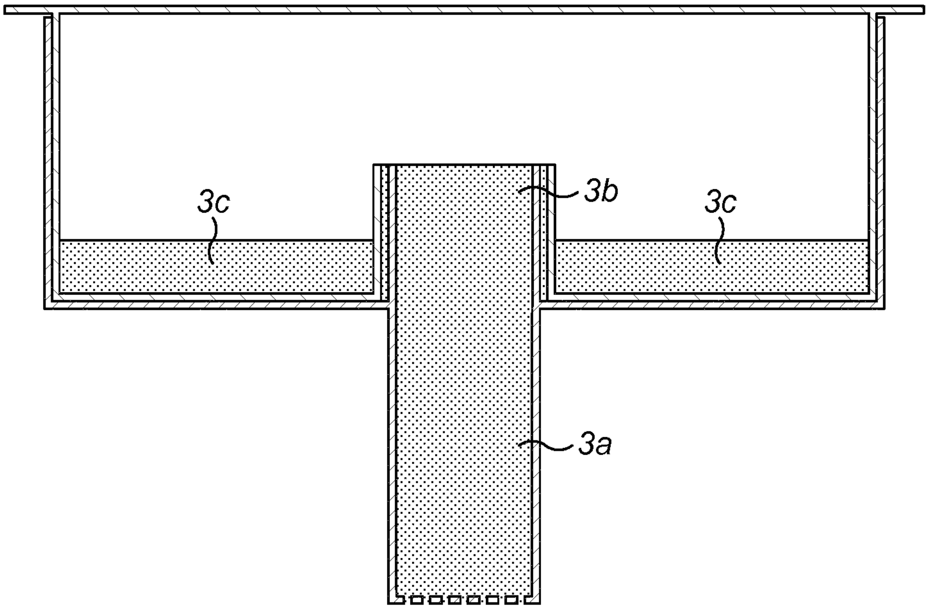
Figure 4:
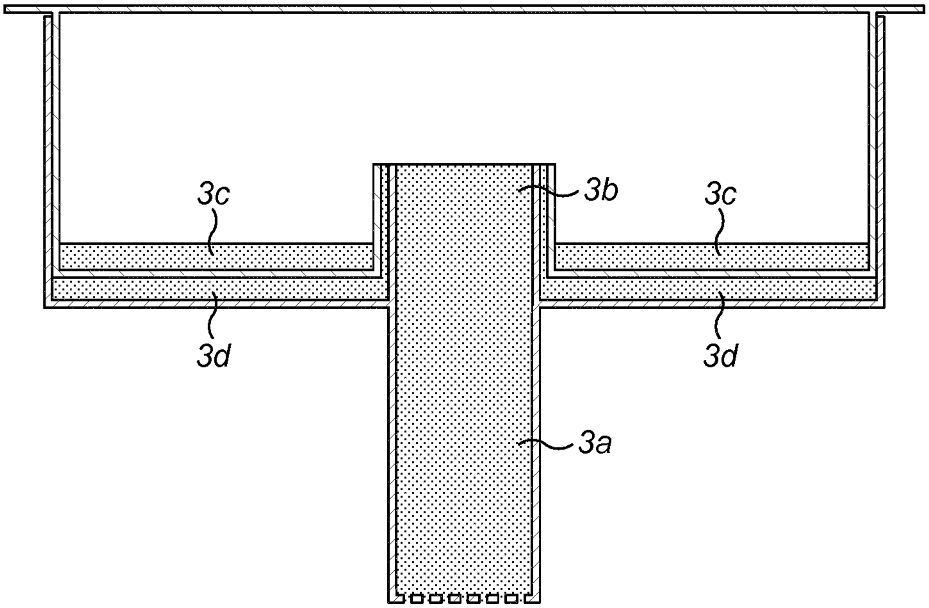

The plunger is also annular (when viewed from above) and corresponds to the size and shape of the filling chamber, so that they form a close fit when the plunger is inserted. Nonetheless, there is a small gap 26 between inner walls 12, 22 of the filling chamber and plunger through which the liquid displaced from the filling chamber flows. The gap may be from 0.1 to 0.2 mm in size, such as about 0.15 mm. The top of the inner wall 12 of the filling chamber and the top of the inner wall 22 of the plunger 20 are at the same height when the plunger is fully inserted, as shown in FIG. 3.

The plunger has a lid 27 which covers the top of the overflow chamber 25. The lid hides the excess liquid from the user after nebulization. In contrast, in the known dosing systems described above, the excess liquid is visible to the user once the plunger is been removed after nebulization. The presence of visible liquid may confuse the user, who may think that this liquid should have been nebulized, and who therefore may be tempted to try to pour the excess liquid back into the filling chamber, and hence dose more than the correct amount.

The dosing system operates as follows. The liquid 3 is poured into the filling chamber 10, for example from a cartridge or ampoule (FIG. 1). The inner wall 12 prevents liquid from flowing directly into the reservoir chamber 31. When the plunger 20 is inserted (FIG. 2), some of the liquid in the filling chamber 10 is displaced through the gap 26 between the inner walls of the filling chamber and plunger, over the filling chamber inner wall 12, through the outlet opening 14 and into the reservoir chamber 31. Once the reservoir chamber 31 and the central space 15 inside the inner wall 12 of the filling chamber is full of liquid (3*a*, 3*b* respectively), the remaining liquid in the filling chamber 10 is displaced over the inner wall 22 of the plunger 20 and into the overflow chamber 25. Once the plunger has been fully inserted (FIG. 3), if a small residual amount of liquid (e.g. the liquid from the gap 26) remains in the filling chamber, it is prevented by the inner wall 12 from entering the reservoir chamber 31 and therefore being inadvertently nebulized. The liquid 3*a* in the reservoir chamber 31 together with the liquid 3*b* in the central space 15 is available to be nebulized.

The excess liquid 3*c* is isolated and retained in the overflow chamber 25, and cannot be nebulized. The dosing system thus dispenses a metered volume of liquid (3*a*+3*b*) to the aerosol generator.

After nebulization has been completed, the excess liquid is poured out of the overflow chamber. The dosing system can then be rinsed out before the next use. The plunger, filling chamber or the whole dosing system may be removable from the nebulizer device so that it can be cleaned by the user, for example rinsed with water and/or placed into a dishwasher.

Figure 2:
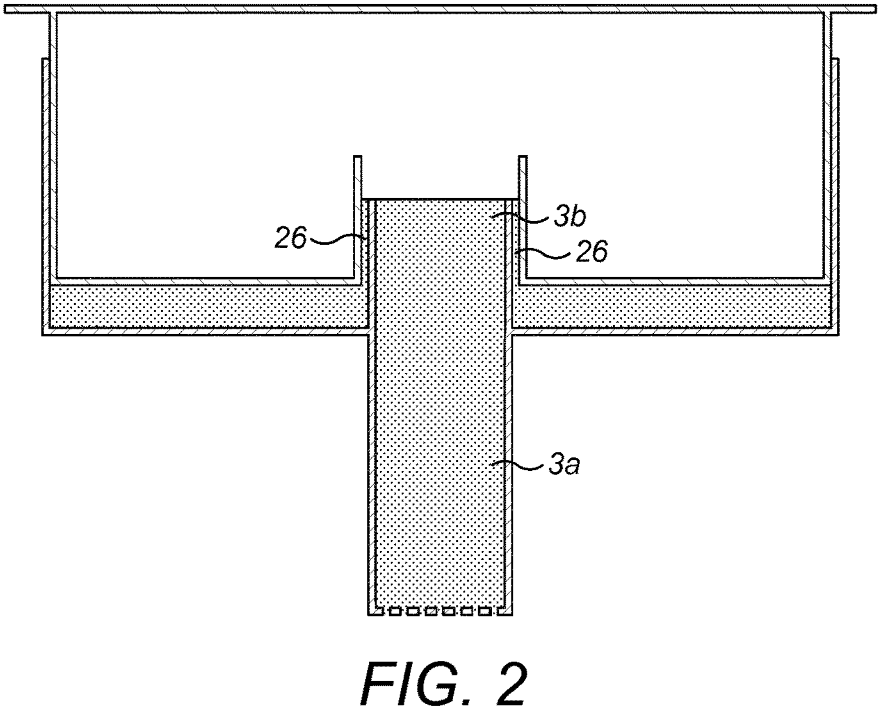

In FIGS. 1 to 3, the plunger 20 occupies essentially the whole of the filling chamber 10 when fully inserted (apart from the gap 26), so that little or no residual liquid remains in the filling chamber. In a variant shown in FIG. 4, the plunger 20 occupies less than the whole volume of the filling chamber 10 when fully inserted so that a portion of the excess liquid 3*c* is displaced into the overflow chamber, whilst another residual portion 3*d* remains in the filling chamber. This residual liquid 3*d* is prevented by the inner wall 12 from entering the reservoir chamber 31 during nebulization. However, this is less preferred, as after nebulization has been completed, the user may see the liquid 3*d* remaining in the filling chamber and think that it should have been nebulized.

In the schematic views of FIGS. 1 to 4, the plunger is shown as being inserted linearly downwards into the filling chamber for simplicity. However, in the dosing system of the invention, shown in FIGS. 5 to 9, the plunger is inserted and removed by a pivoting motion about a hinge 50. This results in the plunger being inserted at a slight angle. Consequently, parts of the walls of the plunger and filling chamber are shaped as appropriate matching curves. The connection between the plunger and the hinge may be designed to allow an easy exchange of the plunger, while at the same time preventing accidental loss of the plunger.

Figure 5A:
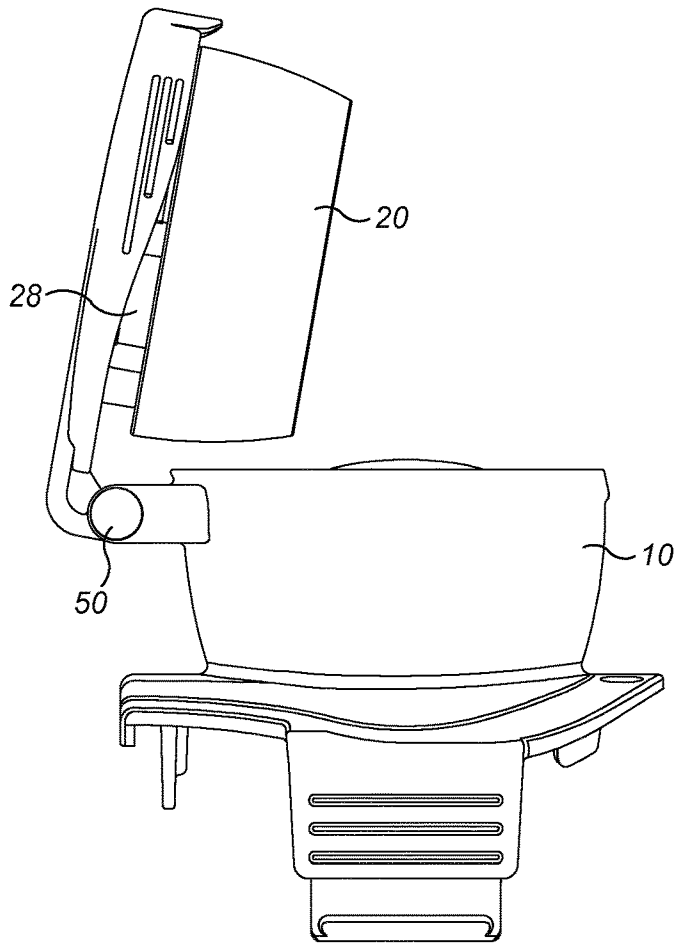
FIG. 5 shows side views of a dosing system according to the invention before and after the plunger is inserted into the filling chamber
Figure 5B:
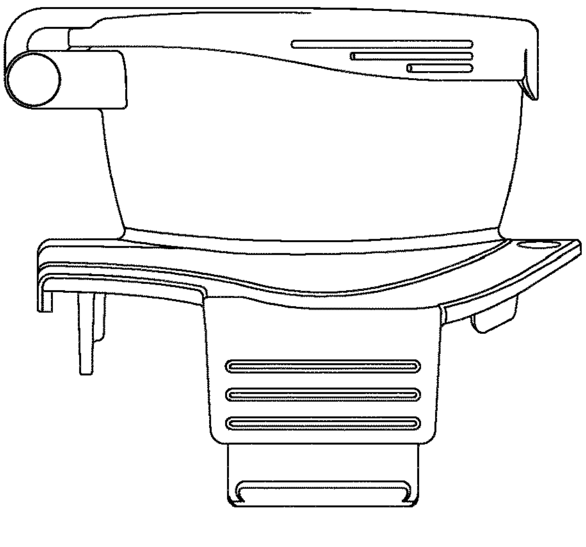
Figure 6A:
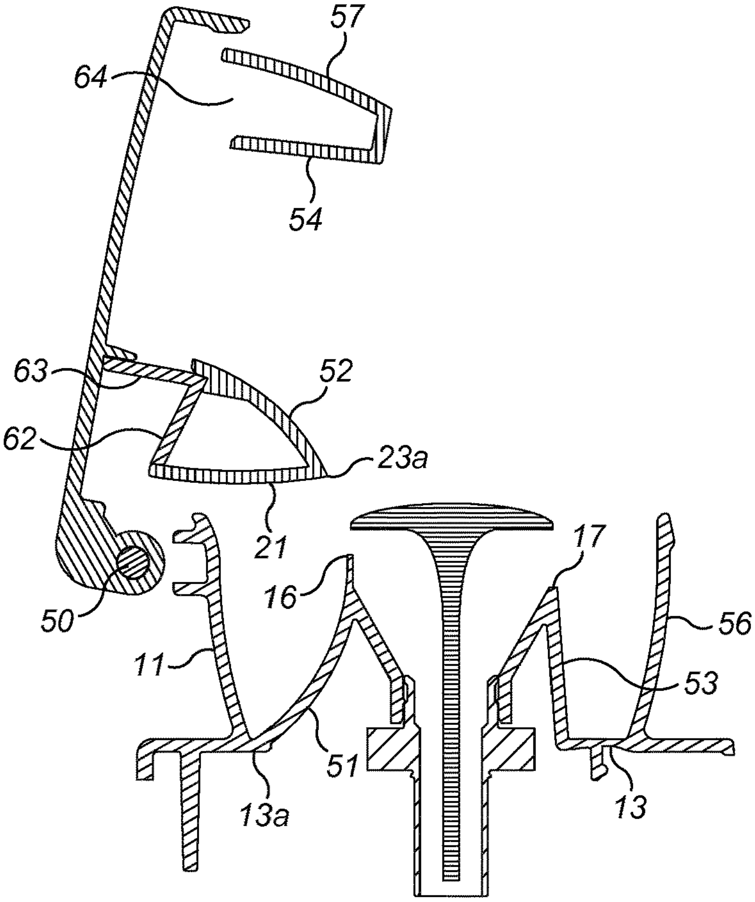
FIG. 6 shows cross-sectional views which correspond to the side views of FIG. 5
Figure 6B:
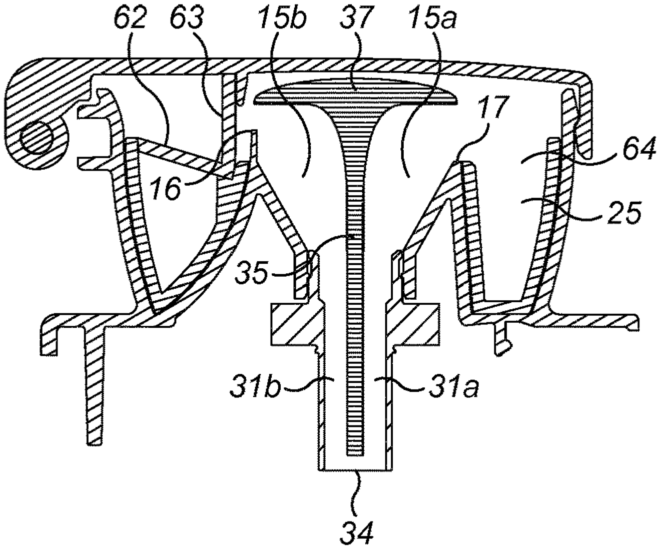
Figure 7:
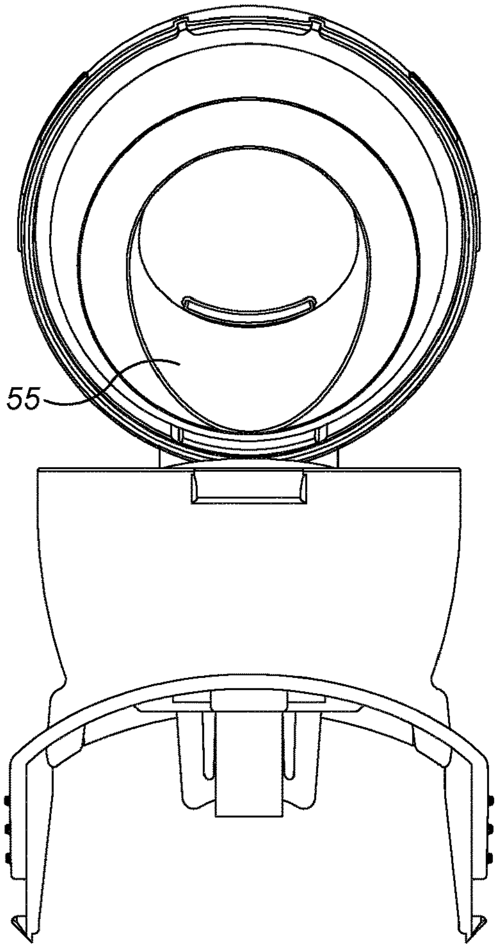
FIG. 7 shows a front view of the dosing system of FIG. 5 before the plunger is inserted into the filling chamber
Figure 8:
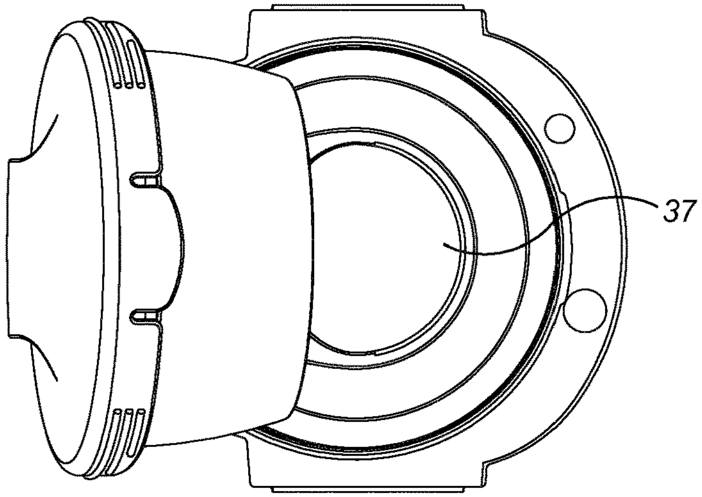
FIG. 8 shows a corresponding view of the dosing system of FIG. 5 from above
Figure 9:
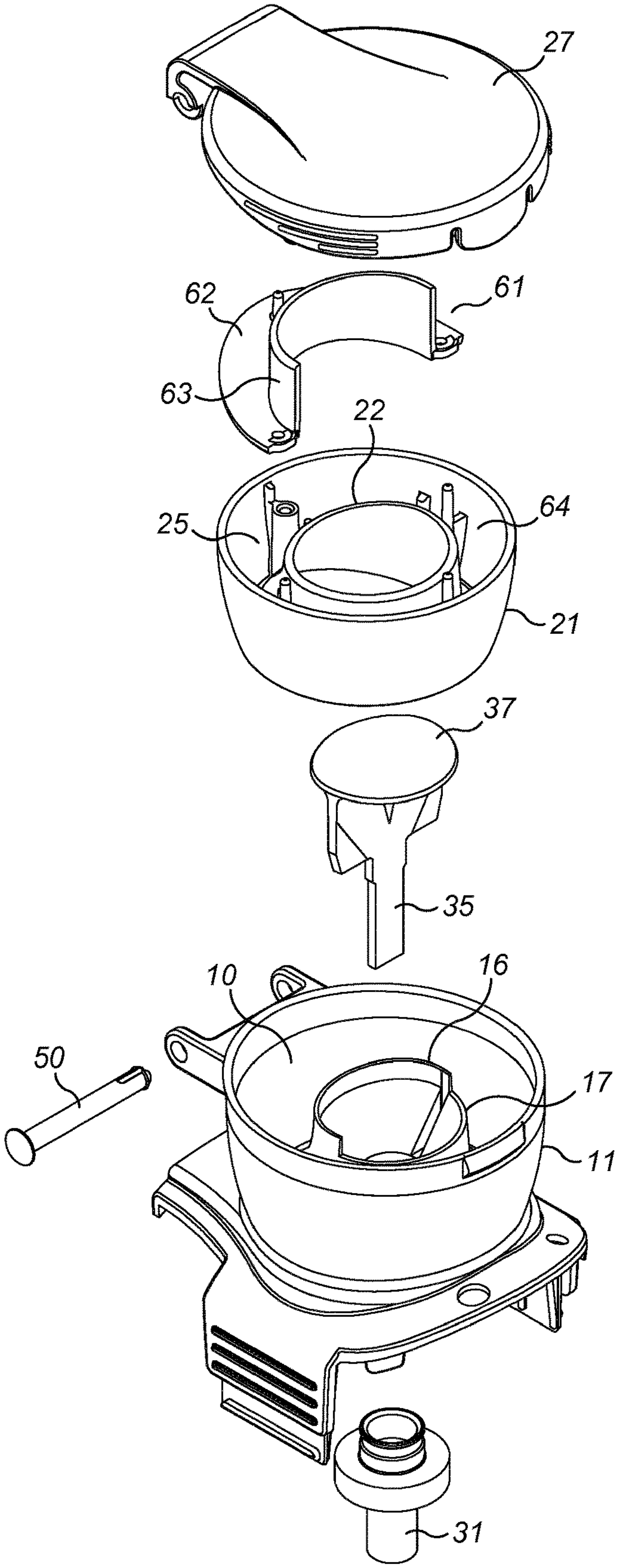
FIG. 9 is an expanded view showing the components of the dosing system of FIG. 5
Figure 10B:
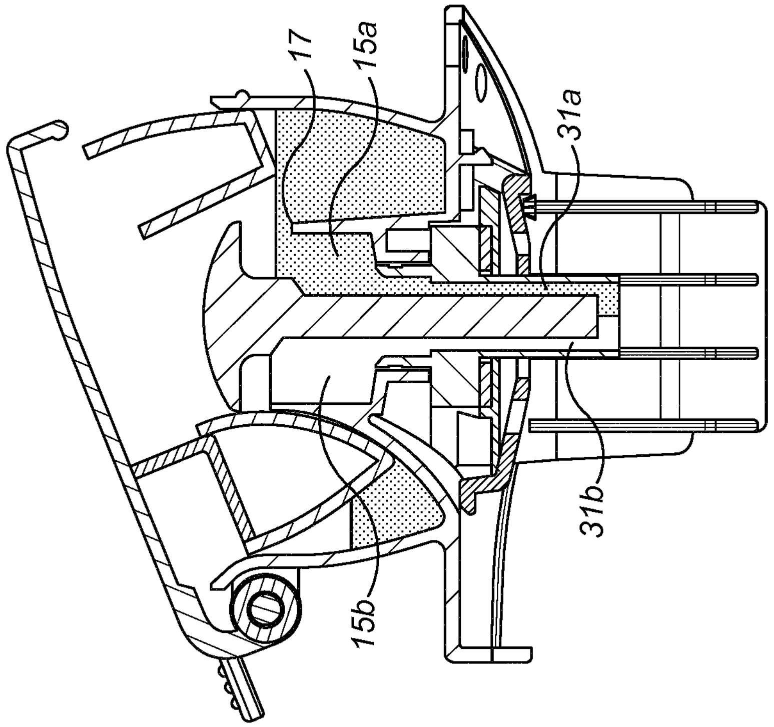
FIG. 10 shows the operation of the dosing system of FIG. 5
Figure 10A:
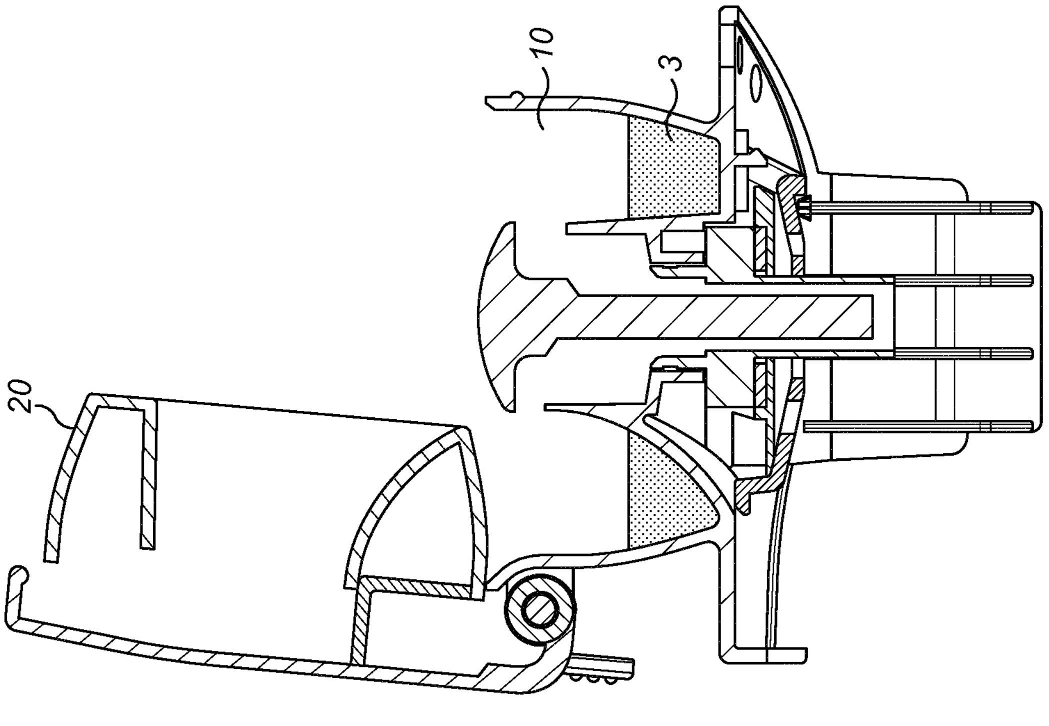
Figure 10D:
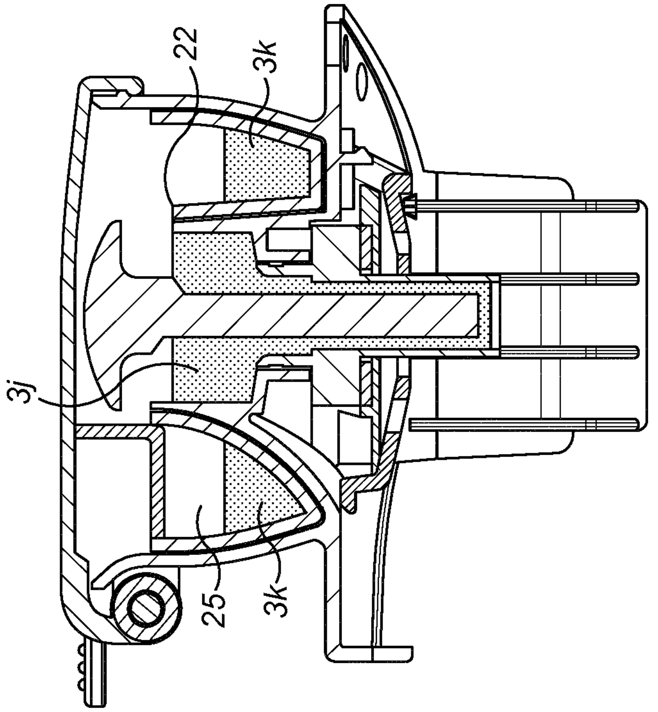
Figure 10C:
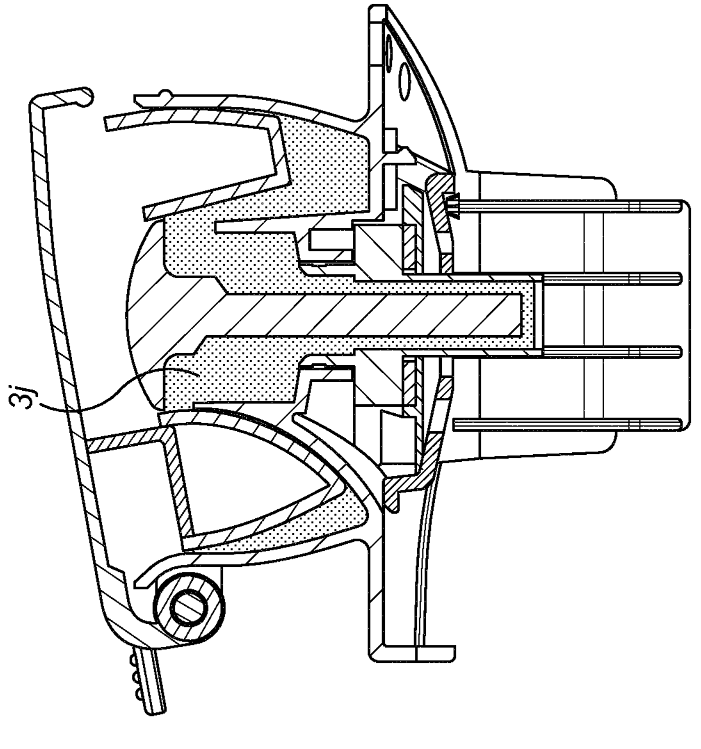

FIGS. 5A and 5B show side views before and after the plunger 20 is inserted into the filling chamber 10 respectively. FIGS. 6A and 6B show the corresponding cross-sectional views. FIGS. 7 and 8 are views of the dosing system in the open position (i.e. before insertion of the plunger) from the front and from above respectively. FIG. 9 is an expanded view showing the components of the dosing system.

As can be seen in FIG. 6B, the inner walls of the filling chamber and the plunger are curved 51, 52 in the region close to the hinge 50, so that the plunger can be pivoted into the filling chamber whilst also ensuring a close fit between the inner walls when the plunger is fully inserted. Nonetheless, the plunger does not need to form a pressure-tight seal with the filling chamber, and indeed intentionally does not do so, in order to provide a gap through which the liquid displaced from the filling chamber can flow.

Moreover, since there is no need for a seal, unlike the dosing systems of WO 2015/022436, the plunger and/or filling chamber do not need to be made from flexible materials, nor are additional components, such as O rings, required. Thus the construction of the dosing system is simplified. Conveniently therefore, the plunger and filling chamber are made from a rigid material, preferably a rigid plastic material.

As a result of the curvature, the bottom of the curved part 51 of the inner wall of the filling chamber meets the outer wall 11 on the side closest to the hinge (shown in FIG. 6A), so that it also effectively forms the base 13*a* of the filling chamber in this region. Correspondingly, the bottom of the curved part 52 of the inner wall of the plunger also meets the outer wall 21 on the side closest to the hinge and forms the base of the plunger 23*a* in this region. Thus the curved part of the inner wall of the plunger 52 forms a cut-away region 55 in the annular shape of the plunger, as shown in FIG. 7. In contrast, the inner walls of the filling chamber and the plunger are not constrained by the pivoting motion on the side opposite the hinge 53, 54, and therefore can be straight.

The outer wall 11 of the filling chamber and the outer wall 21 of the plunger are curved in their respective regions 56, 57 where they are furthest from the hinge 50 for the same reasons. Since they are further from the hinge, the radius of curvature is greater for the curved regions 56, 57 of the outer walls than for the curved regions 51, 52 of the inner walls. Although not necessary for the pivoting motion, the outer walls may have the same curvature everywhere for simplicity and aesthetic appearance. Thus, as shown in FIG. 9, the outer walls 11, 21 of the filling chamber and plunger are both curved, with a small increase in diameter from the base to the top as a result of the shaping.

Inserting the plunger too rapidly could cause liquid to splash out of the filling chamber, rather than steadily displacing it into the reservoir chamber and overflow chamber. In order to prevent this, the hinge may be provided with a detent mechanism which resists the pivoting motion of the plunger. The detent mechanism may operate over the whole pivoting motion, or only in the latter part, i.e. as the plunger comes into contact with the liquid in the filling chamber. The detent mechanism may be any mechanism which is capable of applying a biasing force to the plunger, e.g. a spring or a cam follower associated with the plunger and a corresponding track associated with the filling chamber.

Due to the pivoting motion, the overflow chamber is rotated through approximately 90 degrees when the plunger is moved back into the open position after nebulization. In order to prevent the excess liquid from flowing out of the overflow chamber in this position, there is a cover 61 between the inner 22 and outer 21 walls on the side adjacent to the hinge, visible in FIGS. 6 and 9. The cover comprises a semi-annular floor 62 and a corresponding semi-annular wall 63.

When the overflow chamber 25 is in the open position (FIG. 6A), the cover floor 62 is in a generally vertical orientation. The cover floor must close enough of the overflow chamber so that the liquid cannot flow out when the plunger is pivoted into the open position. For example, as is apparent from FIG. 9, the cover 61 suitably closes the top of the overflow chamber 25 on the side adjacent to the hinge 50 to prevent liquid from flowing out of the overflow chamber, whereas the other side 64 is uncovered.

The filling chamber inner wall is higher 16 on the side adjacent to the hinge than on the opposite side 17 (see FIGS. 6 and 9). Thus when the plunger is inserted, excess liquid is displaced over the lower side 17 of the filling chamber inner wall and enters the open (uncovered) region 64 of the overflow chamber on the side opposite the hinge. Liquid may also be displaced upwards between the filling chamber outer wall and the overflow chamber outer wall. In order to ensure that this liquid does not seep out of the dosing system, the filling chamber outer wall 11 is higher than the overflow chamber outer wall 21, as shown in FIG. 6B.

The higher part 16 of the filling chamber inner wall, together with the cover wall 63 prevents liquid from flowing onto the top of the cover floor 62, or at least minimizes the amount of liquid that does so. Nonetheless, the cover floor 62 is not exactly horizontal (in the closed position) but instead slopes downwardly away from the hinge 50. Consequently any liquid which passes over or round the higher part of the filling chamber inner wall, or over the filling chamber outer wall, and onto the top of the cover floor 62, is guided back down the slope towards the open (uncovered) region 64 and into the overflow chamber 25.

The plunger 20 has a fixed lid 27 which covers the top of the overflow chamber 25, so that the user cannot put the liquid directly into the overflow chamber by mistake. The plunger has an overflow chamber outlet opening 28, shown in FIG. 5, which extends around the whole circumference of the outer wall without a spout. The outlet opening 28 makes it possible, but somewhat awkward, for the user to pour the excess liquid out of the overflow chamber after nebulization has been completed, in order to emphasize that the excess liquid is not intended to be re-used.

Alternatively, the lid may be separable from the overflow chamber in order to facilitate emptying and cleaning of the overflow chamber after use. For example, the lid and overflow chamber may be separately pivotable. The overflow chamber and lid may have clip formations so that when the lid is closed, it becomes attached to the overflow chamber. Thus, after nebulization has been completed, the lid and overflow chamber are pivoted together, and the excess liquid in the overflow chamber is not visible to the user. When the plunger is in the open position, the clip formations can be detached from each other, so that the user can then open the lid, in order to pour out the excess liquid and clean the overflow chamber. The action of having to unclip the lid before pouring out the excess liquid acts as a reminder to the user that the excess liquid is not intended to be re-used.

The whole dosing system can be removed from the nebulizer so that the filling chamber, overflow chamber and reservoir chamber can be cleaned by the user, for example rinsed with water and/or placed into a dishwasher.

As shown in FIGS. 6 and 9, the central space 15 inside the inner wall of the filling chamber is divided by a partition 35 which is parallel to the hinge and extends vertically down into the reservoir chamber 31, thereby separating the central space 15 and reservoir chamber 31 into two parts (15*a*, 31*a* and 15*b*, 31*b* respectively). The partition however does not extend all the way to the membrane 34, so that the reservoir chamber is not divided at the bottom. Since the inner wall of the filling chamber is higher 16 on one side of the partition, and lower 17 on the other, the liquid which is displaced from the filling chamber 10 when the plunger 20 is inserted flows over the lower part 17 of the inner wall and down the corresponding side of the central space 15*a* and reservoir chamber 31*a* to the bottom of the reservoir chamber 31. At the same time, air is displaced upwards on the other side of the reservoir chamber 31*b* and the central space 15*b*, and over the higher part 16 of the inner wall. This prevents the formation of an airlock, i.e. a trapped bubble of air at the bottom of the reservoir chamber.

The partition 35 occupies part of the volume defined by the reservoir chamber 31 and the central space 15, and thus reduces the free volume which can be occupied by the liquid. The volume of liquid dispensed is given by the volume of the reservoir chamber plus the volume of the central space up to the lower part of the filling chamber wall minus the volume of these which is occupied by the partition. The partition therefore provides a further advantage, namely the ability to dispense smaller volumes of liquid than would otherwise be possible. The thickness and or length of the partition can be chosen according to the desired volume of liquid to be nebulized.

The central space 15 inside the filling chamber inner wall 12 may be covered with a cap 37 (see FIGS. 6, 8 and 9). This prevents the user from dosing liquid directly into the reservoir chamber 31 whilst allowing liquid to be dosed into the filling chamber. Consequently (and unlike those dosing systems of WO 2015/022436 in which there is a fixed barrier between the filling chamber and the reservoir chamber), there is no need for a mechanism (such as a safety plunger) to prevent accidental overfilling of the reservoir chamber. Conveniently, the cap 37 can be formed as an extension of the partition 35.

FIG. 10 shows the dosing system of FIGS. 5 to 9 in operation. In FIG. 10A, the plunger 20 is in the open position and the filling chamber 10 contains liquid 3. In FIG. 10B, the plunger 20 has been partly closed and partially inserted into the filling chamber 10, so that it has displaced some of the liquid 3 over the lower side of the inner wall 17 and into the central space 15*a*, from where it flows down into the reservoir chamber 31*a*. Air is displaced up the other side 31*b*, 15*b*. As the plunger is pivoted further into the filling chamber, the central space and reservoir chamber are filled with liquid 3*j*, shown in FIG. 10C. Thereafter, the remaining (i.e. excess) liquid 3*k* is displaced from the filling chamber over the plunger inner wall 22 and into the overflow chamber 25 until the plunger has been completely inserted, shown in FIG. 10D.

Figure 11:
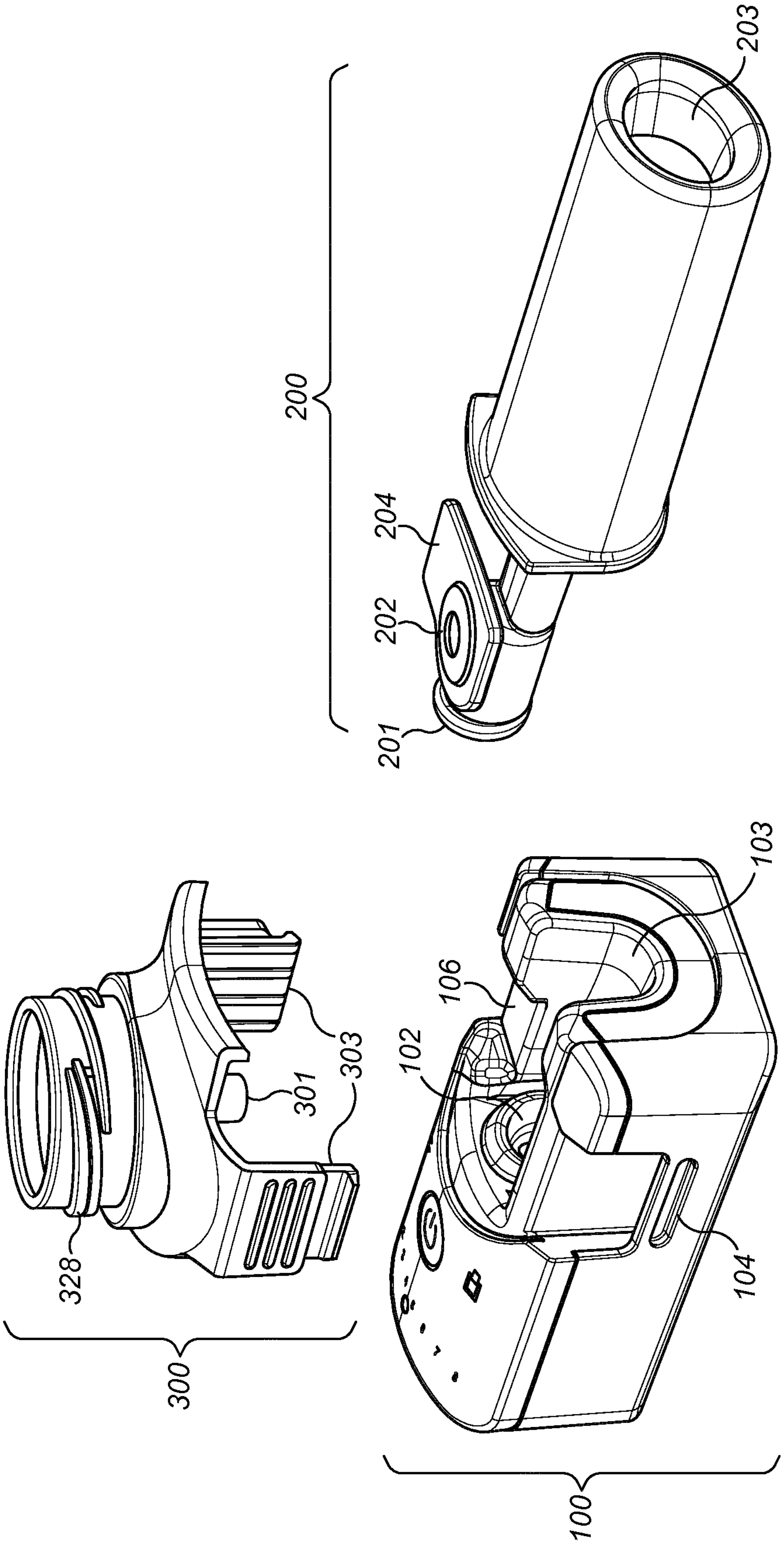
FIG. 11 shows a nebulizer device

The dosing system is suitable for use with the nebulizer device shown in FIG. 11, which is described in detail in EP 2 724 741. The device comprises three parts: a base unit, a mouthpiece, and an aerosol head. The base unit 100 has one or more air inlet opening(s), an air outlet opening 102, a groove 103 for receiving the mouthpiece 200, and one or more key lock members 104. The mouthpiece 200 has an air inlet opening 201 which is attachable to the air outlet opening 102 of the base unit 100, a lateral opening 202 for receiving an aerosol generator 301, and an aerosol outlet opening 203. The mouthpiece 200 is insertable into the groove 103 of the base unit 100. The aerosol head 300 has an aerosol generator 301 and one or more key lock members 303 complementary to the key lock members 104 of the base unit 100. In FIG. 11, the dosing system is not shown, but may be attached to the aerosol head 300 by means of a screw thread 328.

The base unit 100, the mouthpiece 200 and the aerosol head 300 are detachably connectible with one another. The device is assembled by inserting the mouthpiece 200 into the groove 103 in the base unit 100, then placing the aerosol head 300 over the mouthpiece 200 and engaging the key lock member(s) 303 of the aerosol head 300 with the complementary member(s) 104 of the base unit 100 by gentle pressure on both the aerosol head and the base unit. The aerosol generator 301 is positioned in the aerosol head 300 in such a way that when engaging the key lock member (s), the aerosol generator 301 is inserted into the lateral opening 202 of the mouthpiece 200. This creates airtight connections between the aerosol generator 301 and the lateral opening 202 in the mouthpiece as well as between the air outlet opening 102 of the base unit 100 and the air inlet opening 201 of the mouthpiece 200. The base unit 100, the mouthpiece 200 and the aerosol head 300 can be separated by reversing these steps.

The base unit 100 may have one or more indentation(s) 106 whose position may be at or near the groove 103, and the mouthpiece 200 may have one or more positioning member(s) 204. The indentation(s) of the base unit are complementary to (i.e. shaped to receive) the positioning member (s) 204 of the mouthpiece 200. In this context, an indentation is a depression (e.g. a recess, pit, cavity, void, notch or the like) whose "negative" shape is complementary to the "positive" shape of a positioning member (which may be a flange, projection, nose, bulge or the like). Together, such indentations and positioning members act to position the mouthpiece correctly in the base unit. The indentation(s) 106 and the positioning member(s) 204 may be asymmetrical, so as to ensure that the mouthpiece 200 can only be inserted into the indentation 106 of the base unit 100 in one particular manner. This ensures that the device is assembled in such a way that the position and orientation of the mouthpiece 200 and base unit 100 relative to each other are correct.

Figure 12:
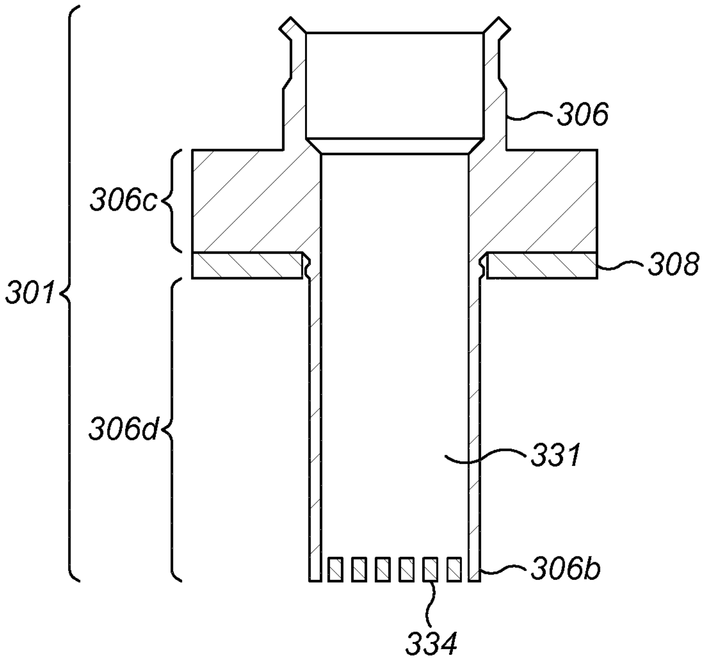
FIG. 12 shows the aerosol generator of the nebulizer device of FIG. 11

The aerosol generator 301 is preferably an ultrasonic liquid atomiser comprising a piezoelectric member 308 and a transducer body 306 as shown in FIG. 12 and described in WO 2008/058941. The transducer body 306 is made of e.g. stainless steel, titanium or aluminium, and encloses the reservoir chamber 331. The reservoir chamber 331 is connected to the dosing system (not shown in FIG. 12) so as to receive liquid to be nebulized from it.

The piezoelectric member 308 is preferably an annular single or multilayer ceramic, which vibrates the transducer body 306 in a longitudinal mode, at a frequency preferably in the 50 to 200 kHz range. As a result, micronic longitudinal displacements, or deformations, occur in a direction parallel to the symmetry axis of the transducer body 306. The transducer body 306 has a region close to the piezoelectric member 308 with a relatively large wall thickness, which serves as a stress concentration zone 306*c*, and a region downstream thereof 306*d* with a relatively low wall thickness which serves as a deformation amplification zone. In this configuration, the vibrations or deformations of the transducer body 306 caused by the piezoelectric member 308 are amplified. Preferably, the piezoelectric member 308 is located at the level of, or adjacent to, the stress concentration zone 306*c*. The internal diameter of the transducer body 306 at the deformation amplification zone 306*d* may be the same as at the stress concentration zone 306*c*, so that the differences in wall thickness correspond to different external diameters. Alternatively, the external diameter of the transducer body 306 may be constant, while the inner diameters differ at the position of the two zones.

A perforated membrane 334 is positioned at the downstream end 306*b* of the transducer body 306. The holes may be formed by electroforming or by laser drilling, with openings normally being in the range from about 1 μm to about 10 μm. Without vibration of the membrane, the balance of pressures, the shape of the holes and the nature of the material used for the membrane are such that the liquid does not seep out through the membrane. However, vibration of the membrane leads to the formation and emission of aerosol droplets through the holes. The membrane may be made of plastic, silicon, ceramic or more preferably metal, and may be affixed to the downstream end 306*b* of the aerosol generator 301 by various means, such as gluing, brazing, crimping or laser welding. Optionally, the membrane at least partially forms a dome in its central region, which causes the jet of nascent aerosol droplets to diverge and hence reduces the risk of droplet coalescence.

Once a treatment operation has been completed, the aerosol head key lock members 303 are disengaged from the complementary member(s) 104 of the base unit, so that the aerosol generator 301 can be removed from the lateral opening 202 of the mouthpiece.

A patient may receive two (or more) different drugs, which will generally require different volumes of liquid to be dispensed, and different aerosolisation parameters, such as droplet size, treatment time etc. Thus a patient may have two (or more) different nebulization devices which are adapted for the different drugs. The first aerosol head has a dosing system designed to dispense the appropriate volume of liquid and the first base unit is configured to provide the appropriate aerosolisation parameters for the first drug. Similarly the second aerosol head and base unit are configured to dispense and aerosolize the second drug. A recognition system can be provided to ensure that the patient uses the correct combinations of aerosol head and base unit. The recognition system could be, for example, based on RFID tags, electrical contacts or mechanical interlock.

A simple mechanical recognition system consists of complementary male and female features on the aerosol head and base unit, for example, one or more cavities/holes on the aerosol head and corresponding protrusions/pegs on the base unit. These may be present in one or more locations and/or sizes and/or shapes selected from a pre-determined number of locations and/or sizes and/or shapes. Conveniently, the complementary features can be located on or formed as part of the key lock members 104, 303. Alternatively the complementary features may be on other parts of the aerosol head and base unit.

Figure 13A:
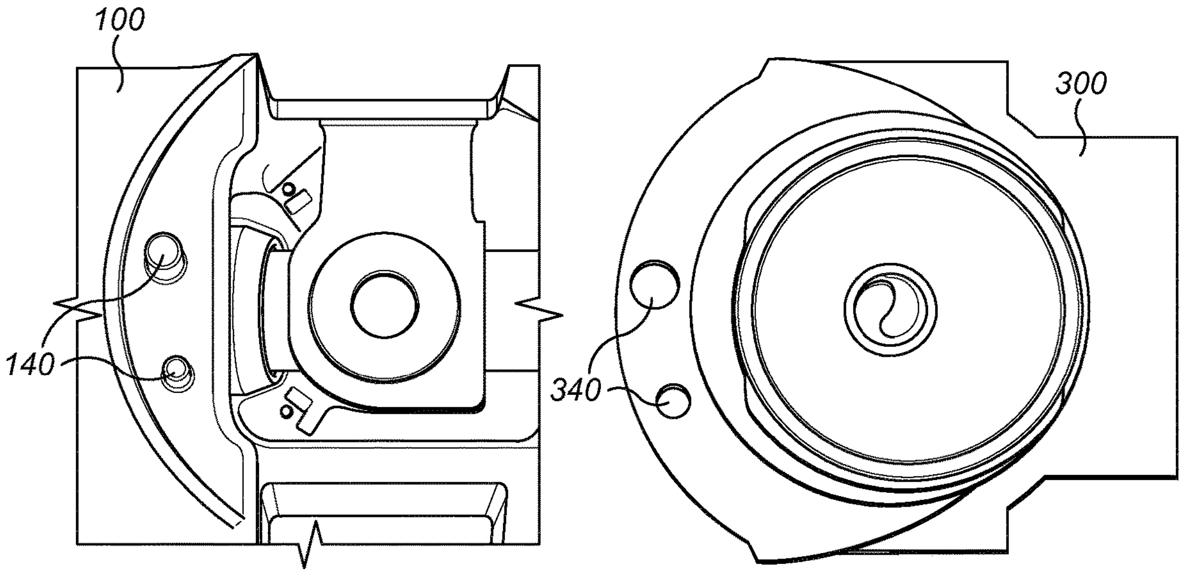
FIG. 13 shows a recognition system for the nebulizer device of FIG. 11
Figure 13B:
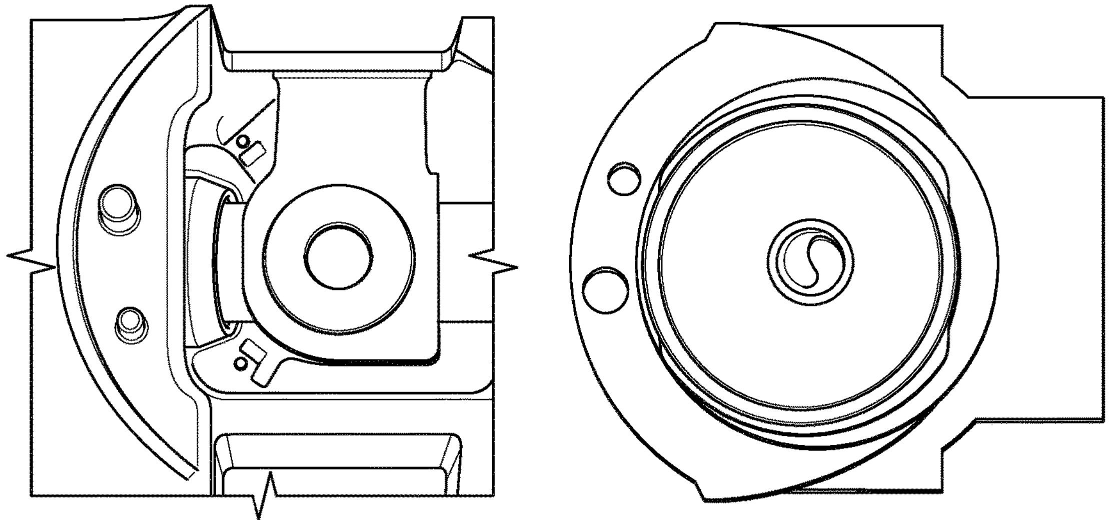
Figure 13C:
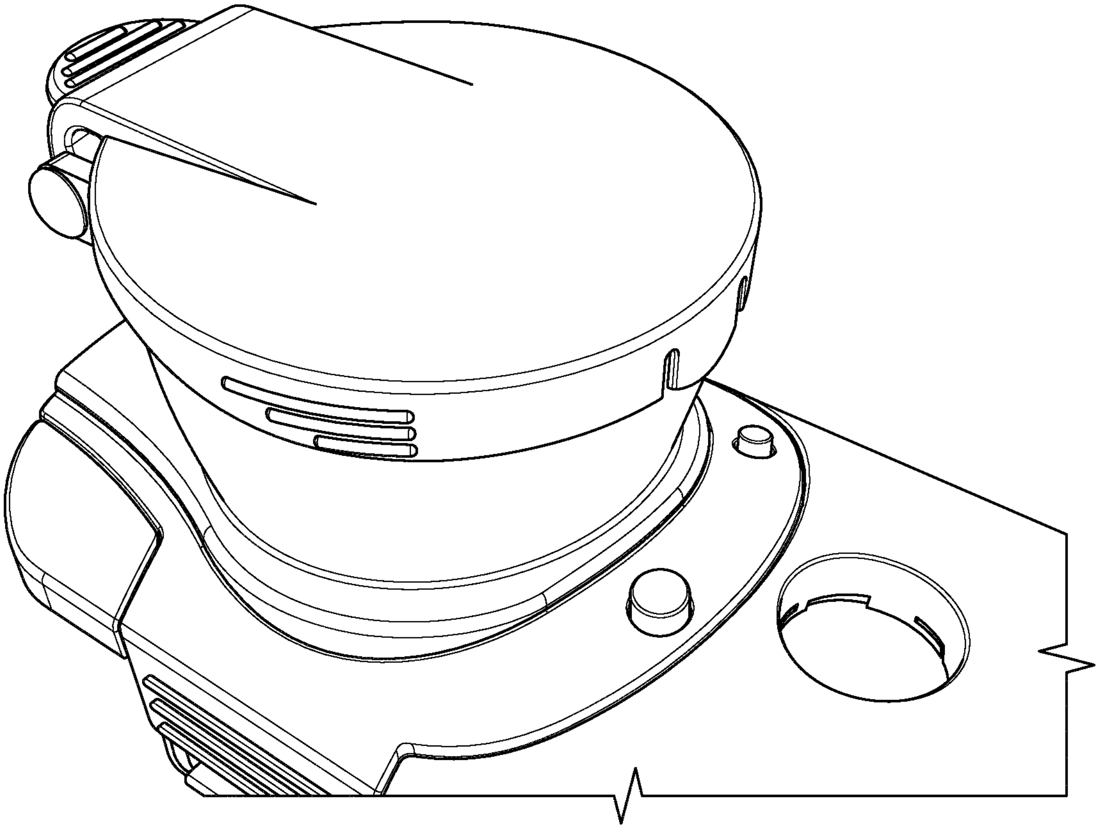

FIG. 13 shows an example of a recognition system which has several (e.g. five) potential hole locations on the aerosol head 300 and corresponding potential peg locations on the base unit 100. Each hole and peg can be either large or small, in order to maximise the number of possible variants for a given number of potential locations. In each variant, two holes 340 are present, one large and one small. The base unit 100 has two pegs 140, also one large and one small. If the locations and sizes of the holes and pegs match (FIG. 13A) then the aerosol head interlocks with, and fits onto, the base unit (FIG. 13C). An advantage of this system is that the pegs and holes are visible, so that the user can easily judge whether the aerosol head and base unit will fit together, i.e. are complementary. Nevertheless, if the user does attempt to use an incorrect aerosol head for the base unit, then the pegs do not match the holes (FIG. 13B). In this event, the pegs 140 hold the aerosol head 300 slightly apart from the base unit 100 which prevents the respective key lock members from interlocking with each other. Thus the recognition system provides both a strong visual cue for the correct combination of the aerosol head and base unit, and also a failsafe mechanism which prevents incorrect combinations from being formed.

The invention claimed is:

1. A dosing system for an inhalation device, comprising:

(a) a filling chamber for receiving a liquid to be aerosolized, the filling chamber having a first outer wall, a base and a first inner wall, the filling chamber further having an outlet opening which is defined by the inner wall of the filling chamber, (b) a reservoir chamber for supplying the liquid to an aerosol generator positioned at a first end of the filling chamber, wherein the reservoir chamber is operatively connected to the outlet opening, and (c) a plunger which is mounted on a hinge which includes an overflow chamber, said plunger being configured to be inserted into the filling chamber and said overflow chamber being configured to receive at least a portion of the liquid from the filling chamber when the plunger is inserted into the filling chamber, wherein a first portion of the inner wall of the filling chamber proximate to the hinge is higher than a second portion of the inner wall of the filling chamber distal from the hinge with respect to the first portion of the inner wall of the filling chamber so that when the filling chamber is filled with liquid and the plunger is inserted into the filling chamber by pivoting the plunger about the hinge, part of the liquid is displaced by the plunger over the second portion of the inner wall of the filling chamber and into the reservoir chamber via the outlet opening, and some or all of the remaining liquid is displaced by the plunger from the filling chamber into the overflow chamber.

2. The dosing system of claim 1, further comprising a cap positioned at a second end of the filling chamber opposite from the first end and configured to obstruct the outlet opening at the second end to prevent the liquid from being supplied directly into the reservoir chamber.

3. The dosing system of claim 2, further comprising a partition located within the outlet opening of the filling chamber, wherein the partition extends into the reservoir chamber, wherein the cap is formed as an extension of the partition.

4. The dosing system of claim 1, wherein the plunger further comprises a second inner wall and a second outer wall, and wherein at least part of the first inner wall and first out wall of the filling chamber and the second inner wall and second outer wall of the plunger are curved.

5. The dosing system of claim 1, further comprising a partition located within the outlet opening of the filling chamber, wherein the partition extends into the reservoir chamber.

6. The dosing system of claim 1, wherein the overflow chamber further comprises a cover which is configured to close the top of the overflow chamber on a side adjacent to the hinge.

7. The dosing system of claim 1, wherein the plunger further comprises a lid.

8. The dosing system of claim 7, further comprising an opening between the lid and a top end of the overflow chamber.

9. The dosing system of claim 7, wherein the overflow chamber and the lid are separately pivotable.

10. The dosing system of claim 9, wherein the overflow chamber and lid each comprise clip formations configured to attach the lid to the overflow chamber when the lid is closed.

11. The dosing system of claim 1, wherein the overflow chamber corresponds to the size and shape of the filling chamber, so that the plunger occupies the whole of the filling chamber when inserted into the filling chamber.

12. The dosing system of claim 1, wherein the filling chamber and the plunger are made from a rigid material.

13. The dosing system of claim 1, wherein the filling chamber and the plunger are made from a rigid plastic.

14. An inhalation device comprising the dosing system of claim 1.

15. The inhalation device of claim 14, further comprising an aerosol head comprising the dosing system and a base unit, wherein the aerosol head and base unit are detachably connected with each other, and wherein the aerosol head and base unit have complementary male and female features which interlock to provide a recognition system.

16. The inhalation device of claim 15, wherein the base unit comprises the male features and the aerosol head comprises the female features, wherein the male features comprise two pegs of different sizes and the female features comprise two holes sized to correspond with the different sizes of the two pegs, respectively.

17. A method for dosing liquid to an inhalation device of claim 14, the method comprising supplying the liquid to be aerosolized to the filling chamber, and inserting the plunger into the filling chamber so that a first part of the liquid is displaced over the first portion of the inner wall of the filling chamber into the reservoir chamber and a second part of the liquid is displaced into the overflow chamber.

* * * * *